Sept. 2, 1958 J. DAVIS Plant Pat. 1,746

PEACH TREE

Filed Feb. 20, 1956

INVENTOR
JONATHAN DAVIS
by Charles R. Fay,
atty.

United States Patent Office

Plant Pat. 1,746
Patented Sept. 2, 1958

1,746

PEACH TREE

Jonathan Davis, Sterling Junction, Mass.

Application February 20, 1956, Serial No. 566,745

1 Claim. (Cl. 47—62)

The present invention or discovery relates to a new and distinct variety of peach tree primarily characterized by its earliness of ripening, color and texture of the flesh of its fruit, the free condition of its stone, and the sharply serrate margin and eglandular condition of its leaves.

This new variety originated at the Davis Farm, Wilder Road, Bolton, Massachusetts, as a sprout from below the bud union on an orchard tree of the unpatented Elberta variety, the top of which had been severely damaged by deer. It is therefore presumed to be a seedling of the unpatented Lovell variety which variety is the most common source of pits from which seedling trees are grown in the nursery row for budding. The remainder of the damaged trees was removed and the sprout treated as the bud. Several seedlings were subsequently budded at the same location from the original tree and produced the same characteristics.

While the sharply serrate margin and the absence of petiolar glands serve to distinguish the trees of this variety from those of practically all other named varieties of peach, its valuable characteristics are, of course, found in the fruit. The fruit of this variety starts to ripen about with the Erly-Red-Fre variety, U. S. Plant Patent No. 320, but have a picking season of about ten days.

Figure 1:
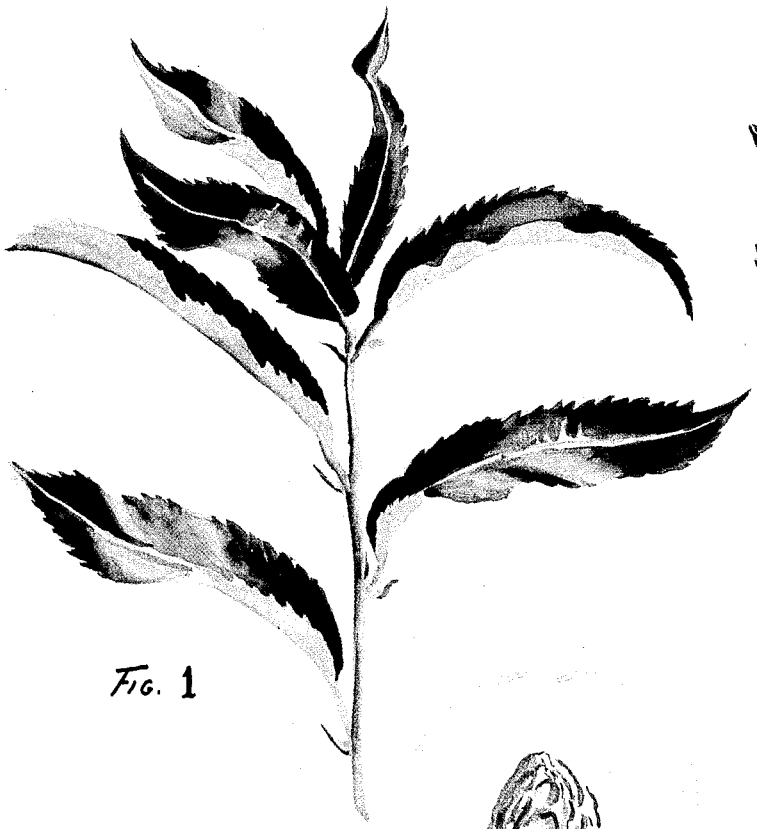
Fig. 1 is a view showing a stem and leaves.
Figure 2:
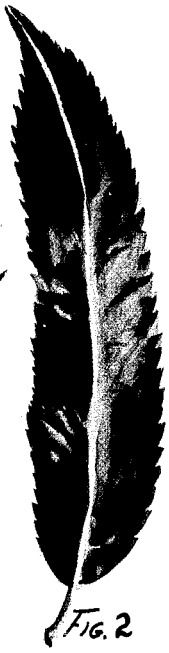
Fig. 2 is a view showing a single leaf.
Figure 3:
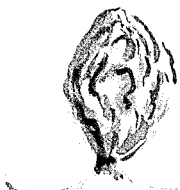
Fig. 3 is a view illustrating the fruit cut and showing the stone.
Figure 4:
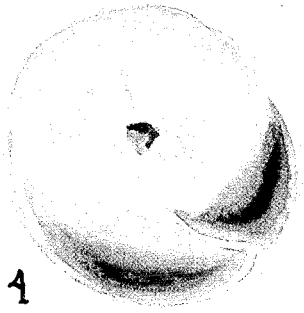
Figs. 4 and 5 are similar views illustrating different aspects of the fruit as it appears in ripened condition.
Figure 5:
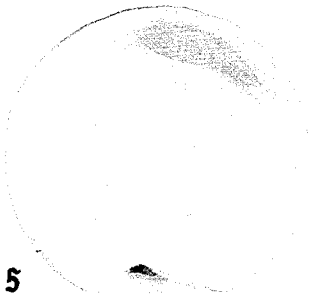

The fine grained flesh of the fruit is uniformly yellow throughout $$\left(1Y \text{ to } 3Y\frac{8.5-9}{8-10}\right)$$

with no red flush around the pit. The medium size stone is essentially free and light brown in color.

$$\left(4.5YR \text{ to } 5.5YR\frac{6-7}{4}\right)$$

The following is a more accurate description of the characteristics of this new variety of peach:

Leaves large, rather dark green $$\left(4GY \text{ to } 6GY\frac{3.5-4.5}{4-6}\right)$$

moderately V-folded, rugose and puckered along the mid-rib with margins considerably waved and having sharply serrate distinct serrations; petioles eglandular.

Flowers are of the non-showy type with medium size petals and appear approximately in concert with the "Erly-Red-Fre."

Fruits regular in form, roundish oval, somewhat compressed opposite the sutures with somewhat unequal halves; cavity deep and rather wide; suture shallow to medium, distinct; apex rounded with a small distinctly depressed tip; skin color yellow $$\left(1Y \text{ to } 3Y\frac{8-8.5}{8-10} \text{ mature}\right)$$

overlaid with red $$\left(6R \text{ to } 8R\frac{4-5}{12-14}\right)$$

where exposed to the sun showing mottling and broad striping on many specimens; pubescence medium in length and thickness; flesh uniformly yellow throughout $$\left(1Y \text{ to } 3Y\ \frac{8.5-9}{8-10}\right)$$

with no red about the pit, fine grained, melting, juicy, sweet and very good quality; stone-free, medium size, averaging slightly larger than "Erly-Red-Fre," oval and plump but flattened near the stem end, with blunt apex and rather coarsely corrugated and pitted surface.

The above description utilizes Munsell Color Notation.

I claim:

A new variety of peach tree substantially as shown and described, characterized by the earliness of ripening of the fruit, the color and texture of the flesh of the fruit, particularly as to uniform yellowness of color and fine grain of the texture, the free condition of the stone, and the serrate margin and eglandular condition of the leaves.

No references cited.